United States Patent [19]

Beavers et al.

[11] Patent Number: 5,148,311
[45] Date of Patent: Sep. 15, 1992

[54] NON-FOGGING TRANSPARENT COATINGS

[75] Inventors: Ellington M. Beavers, Meadowbrook; Karen M. Lowry, Jenkintown, both of Pa.

[73] Assignee: Beacon Research, Inc., Glenside, Pa.

[21] Appl. No.: 717,491

[22] Filed: Jun. 19, 1991

[51] Int. Cl.$^5$ ............................................. A61F 2/16
[52] U.S. Cl. ................................. 359/507; 156/60; 359/642; 427/2; 427/338; 427/164; 427/165; 530/356; 623/6
[58] Field of Search ............... 156/60; 359/507, 642; 427/2, 338, 164, 165; 530/356; 623/6

[56] References Cited

U.S. PATENT DOCUMENTS

| | | | |
|---|---|---|---|
| 4,240,163 | 12/1980 | Gala | 427/2 X |
| 4,459,317 | 7/1984 | Lambert | 427/2 |
| 4,663,233 | 5/1987 | Beavers | 427/164 X |
| 4,801,475 | 1/1989 | Halpern et al. | 427/407.1 X |
| 5,023,114 | 6/1991 | Halpern et al. | 427/340 X |
| 5,037,677 | 8/1991 | Halpern et al. | 427/340 X |

Primary Examiner—Michael Lusignan
Attorney, Agent, or Firm—William H. Eilberg

[57] ABSTRACT

A transparent, hydrophilic, non-fogging coating is applied to the surface of an object. The coating includes a bilaminar graft formed of two films. The first film, denoted the matrix, adheres to the surface of the object, and contains functional groups capable of chemically reacting with a mucopolysaccharide. The second film, denoted the hydrophil, contains the mucopolysaccharide. A quantity of ethylenedinitrilo-tetrakis-(2-hydroxypropane) is added to the matrix and to the hydrophil. Also added to the hydrophil are dimethyl sulfoxide (1%) and desulfated heparin (0.5%). The result is a permanent, transparent, hydrophilic, non-fogging coating. The coating can be formed on an intra-ocular lens or a contact lens, or on other objects. Also, the coating can be formed on a substrate to which the coating does not adhere permanently. The coating can then be separated from the substrate, stored, and later adhered to another surface.

19 Claims, No Drawings

NON-FOGGING TRANSPARENT COATINGS

BACKGROUND OF THE INVENTION

This invention relates to the field of coatings, especially transparent coatings for clear plastic surfaces, such as those used in making intra-ocular lenses and contact lenses.

Transparent plastics and glass are normally hydrophobic and are not wetted uniformly by water, which forms beads and rivulets on the surface and distorts the optical transmission of the lens, prism, or pane. When warm, moisture-laden air impinges on the plastic or glass surface, a film of tiny water droplets condenses thereon and destroys the optical clarity of the transmitted light. The novel, durable coating of the present invention provides uniform light transmission without fogging and eliminates optical distortion in both the wet and dry state.

It is well known that certain water-soluble materials such as glycerine can be wiped or sprayed onto an automobile windshield to prevent beading by raindrops. Scuba divers and deep-sea divers are also familiar with the practice of rubbing sputum on the inner surface of the facepiece or lens in order to delay fogging of the inner surface. However, such measures are only temporary and are therefore unsatisfactory.

Silicone coatings have been claimed to provide more permanent protection against fogging, but side-by-side comparison of coated and uncoated panels shows that the improvement is less than desired. Conditions prescribed for the coating process by vendors are in some cases above the glass temperature of the plastic to be coated and therefore damaging to the optical device. Coatings offered by certain vendors produce devices with mediocre fogging resistance and surprisingly poor optical properties.

Hydrophilic coatings, such as those described in U.S. Pat. No. 4,663,233, for example, are durable and show non-fogging and non-beading behavior when wet, but tend to fog in a cold, dry atmosphere.

As will be shown, the durable coatings of this invention are non-fogging at elevated and low temperatures, and at high and low humidity. This novel and useful characteristic is retained under practical conditions of exposure not just for minutes, but for long periods.

SUMMARY OF THE INVENTION

The present invention includes a method of applying a transparent, hydrophilic, non-fogging coating to an object, the method comprising the following steps. First, one coats the object with a solution of a polymer having a plurality of functional groups capable of chemically reacting with a mucopolysaccharide, and manifesting a high degree of adhesion to the object. The latter solution includes 0.1–10% ethylenedinitrilo-tetrakis-(2-hydroxypropane) (EDITH). Then, the solvent is removed from the solution, so as to form a first continuous film. Next, one applies, as a second coat, an aqueous solution of a mucopolysaccharide, wherein the mucopolysaccharide solution includes about 0.1–5% ethylenedinitrilo-tetrakis-(2-hydroxypropane). The mucopolysaccharide solution also contains about 0.1–1% of desulfated heparin and about 0.1–5% of dimethyl sulfoxide. One then removes water from the second coat, so as to form a second continuous film. Finally, the two films are chemically joined to form an interlaminar graft. The chemical joining can be done by allowing the films to stand for a period of time, or by heating the films.

The invention also includes a structure made according to the method described above. The method can be used to make a coated lens, such as an intra-ocular lens or a contact lens, which has a transparent, hydrophilic, permanent, non-fogging coating. The method can also be used to coat spectacle lenses, face masks, or goggles.

In another aspect of the invention, the coating made according to the above-described method can be formed on a substrate to which the coating does not adhere permanently. The coating can then be removed from the substrate, with the aid of a sharp blade. The separated coating has the form of a flexible sheet which can be stored in a roll. It is also possible to apply an adhesive to one side of the flexible sheet and adhere the sheet to a surface for which one wants to provide a transparent, hydrophilic, non-fogging coating.

It is therefore an object of the invention to provide a method of applying a transparent, permanent, hydrophilic, non-fogging coating to the surface of an article.

It is another object of the invention to provide an article which has the coating described above.

It is another object to provide a lens, such as an intra-ocular lens or a contact lens, which has the coating described above.

It is another object to provide a flexible material which is transparent, hydrophilic, and non-fogging, and which is not attached to a substrate.

It is another object to provide a method of applying a transparent, hydrophilic, non-fogging coating to the surface of a large object.

Other objects and advantages of the invention will be apparent to those skilled in the art, from a reading of the following detailed description of the preferred embodiments, and the appended claims.

DETAILED DESCRIPTION OF THE PREFERRED EMBODIMENTS

This invention comprises an improvement over the hydrophilic, lubricious, durable coatings described in U.S. Pat. Nos. 4,801,475 and 4,663,233, and copending U.S. patent application Ser. Nos. 07/517,482 now U.S. Pat. No. 5,023,114, and 07/436,924, now U.S. Pat. No. 5,037,677, the disclosures of all of which are incorporated by reference herein. The above-mentioned patents and applications describe bilaminar coatings produced by chemically grafting a first reactive coat (denoted the "matrix") to a top coat comprising a mucopolysaccharide (denoted the "hydrophil"). Reference may be made to that art both for operable limits and for specific examples of compositions and processes of application. Repetition of the parameters here will be the minimum required for clarity and illustration.

The method disclosed and claimed in one or more of the above-cited references includes the following steps. First, one coats the object with a solution of a polymer having a plurality of functional groups capable of chemically reacting with a mucopolysaccharide, and manifesting a high degree of adhesion to the object. This first coating is the "matrix". The solvent is removed from the solution, to form a first continuous film. Next, one applies, as a second coating, an aqueous solution of a mucopolysaccharide. This second coating is the "hydrophil". One then removes water from the second coat, so as to form a second continuous film. Finally, the two films are chemically joined to form an interlaminar graft. The chemical joining can be done by allowing the films to stand for a period of time, or by heating the films.

It has been discovered that major improvement in fogging resistance of the coatings is achieved by addition of ethylenedinitrilo-tetrakis-(2-hydroxypropane) to the matrix and to the hydrophil. Also added to the hydrophil are dimethyl sulfoxide (1%) and desulfated heparin (0.5%). Ethylenedinitrilo-tetrakis-(2-hydroxypropane) is available commercially from BASF Corporation, Chemicals Division, of Persippany, N.J. 07054, and is recommended, by the latter company, for use as a chelating agent, as a crosslinking agent in polyurethane manufacture, as a humectant, as a plasticizer, and as a complexing agent. In this disclosure, the compound will be called "EDITH". Also in this disclosure, all percentages are taken by weight.

Most surprising and unpredictable is the durability of the coatings under practical conditions of use. The non-fogging characteristic is not impaired by long soaking in water, despite the ready solubility in water of both dimethyl sulfoxide and EDITH. Substantial improvements in abrasion resistance and ultra-violet light resistance of the coatings containing these additives were not anticipated, but are reproducibly achieved.

The preferred amounts of these additives are about 0.1% to 10% EDITH (preferably about 1%) on the weight of matrix solution (normally 15% to 30% solids in organic solvent) and about 0.1% to 5% EDITH (preferably about 1%) on the weight of hydrophil solution (normally 0.1% to 15% mucopolysaccharide in water). The hydrophil must also contain about 0.1% to 1% of desulfated heparin (preferably 0.5%) and about 0.1% to 5% (preferably 1%) of dimethyl sulfoxide. The solutions may or may not contain other additives also that are familiar to persons skilled in the art of coatings, for purposes not essential to the operation of this invention.

EXAMPLE 1

A 20% solution in 2-methoxypropyl acetate was prepared of a copolymer comprising ethyl methacrylate (84 mole percent), hydroxyethyl methacrylate (15.4 mole percent) and methacrylic acid (0.6 mole percent). This copolymer was converted to a polyisocyanate "prepolymer" by coreaction with a stoichiometric excess of Desmodur N-90, which is commercially available from the Mobay Corporation, of Pittsburgh, PA 15205. To the prepolymer solution was added 1% by weight of EDITH, and the mixture was then knife-coated at 3 mils onto a poly(methyl methacrylate) panel labeled A. Another similar panel (labeled B) was coated with prepolymer solution containing no EDITH.

After evaporation of the solvent, panel B was given a top-coat (nominal 3 mils) of 0.5% sodium hyaluronate in water. The water evaporated under vacuum at 45 C, and the panel was cured at 45 C for 24 hours. Panel A was treated in a similar manner, except that the top-coat solution contained 0.5% desulfated heparin, 1% EDITH, and 1% dimethyl sulfoxide in addition to the sodium hyaluronate.

Panels A and B were stored overnight in a refrigerator at 4° C. When taken out, they were immediately exposed to the technician's breath. Panel B fogged heavily. Panel A remained clear and free of fog on the coated side.

Panels A and B were compared side-by-side in a Gardner abrader under a standard sponge kept wet with distilled water. The Gardner abrader is essentially a device which moves a sponge, or its equivalent, back and forth repeatedly over the surface to be tested. The device moves through 50,000 cycles in about 22 hours, and a counter records the number of cycles. In this Example, Panel B survived 160,500 cycles before lubricity was lost on the worn surface. Panel A survived 354,600 cycles.

Panels A and B were compared side-by-side while mounted on an outdoor rack free of shadows and facing southeast at an angle of 45°. Panel B was losing lubricity after six days of exposure, while Panel A showed no loss after thirty days of exposure.

EXAMPLE 2

Coated panels were prepared and cured in the manner described in Example 1 for Panel B, but in each case with the addition to the hydrophil solution of 1% of known humectants. A separate panel was prepared for each of the following humectants:

Sorbitol
Hydantoin
Hydantoic acid
Hydantoin 5-acetic acid
Equal parts of hydantoin and hydantoic acid
Potassium citrate
Sodium citrate
Sorbitol at various levels ranging from 0.1% to 20%

Not one of the foregoing panels showed a useful degree of fog resistance and coating integrity. Sorbitol, for example, a well-known humectant, caused the coating to become wet, soft, and sticky while effecting no significant improvement in fogging behavior.

This Example demonstrates that behavior of an additive as a humectant does not qualify it a priori as a non-fogging agent in these coatings and that the highly unusual contributions of EDITH and dimethyl sulfoxide were not obviously predictable.

EXAMPLE 3

Durable non-fogging coatings like that for Panel A in Example 1 were applied to acrylic (PMMA) sheet, aluminum, glass mirror, rhodium, and polyester sheet, with good results.

EXAMPLE 4

A matrix polymer was prepared in 2-methoxypropyl acetate having the composition: ethyl methacrylate, 85 mole percent, and isocyanatoethyl methacrylate, 15 mole percent. When used weight-for-weight in place of the Desmodur N-90 prepolymer of Example 1, virtually identical results were obtained as described there.

EXAMPLE 5

Panel A of Example 1 was immersed in water to a depth that covered the lower half of the coated panel. The panel was allowed to stand for two months. At the end of this time, the panel was removed and tested again for fogging tendency as described in Example 1. The entire coated area was fog-resistant, with no difference between soaked and unsoaked areas. This Example shows that the coating endures exposure for long periods to conditions that might be expected to extract a simple humectant and destroy the anti-fogging quality.

The desulfated heparin in the hydrophil can be replaced by other components, such as glucosamine, but the desulfated heparin is preferable, as it yields the best results.

The thicknesses of the coatings applied to the substrate can be varied widely and independently. In general, the more dilute the solution applied to the substrate, the thinner the resulting coating, since the coating is formed from the solids in the solution. To make a thicker coating, one can use a more concentrated solution, and/or one can apply the coating in several subcoats to build up a layer of desired thickness.

Because of the variables described above, the percentages of each component, in the final product, will vary considerably. In one example, the matrix coat was about 0.0015 inches thick, when wet, and the concentration of the matrix solution was 30%. Thus, when dried, the matrix coat was about 0.00045 inches thick. The hydrophil coat, when wet, was about 0.00125 inches thick, and the concentration of the hydrophil solution was 0.5%. Thus, when dried, the hydrophil coat was about $6.2 \times 10^{-6}$ inches thick. The total thickness of the two coats was therefore about $4.562 \times 10^{-4}$ inches. The percentages, by weight, of the components in the final product were approximately as shown below:

| | |
|---|---|
| Matrix polymer | 85% |
| Hyaluronate | 1.7 |
| EDITH | 7 |
| Desulfated heparin | 1.7 |
| Dimethyl sulfoxide | 3.5 |
| Other additives | 1 |

The total is not exactly 100% due to rounding.

Clearly, the percentages of the components will vary considerably if the thicknesses and concentrations of the coats are changed. Thus, the above example should not be deemed to limit the invention. The invention includes many possible compositions.

The method described above can be used to produce coated products having great practical utility. For example, the coating of the present invention can be applied to an intra-ocular lens (IOL) or to a contact lens. In either case, since the outer layer of the bilaminar coating of the present invention is hydrophilic, the coated IOL or contact lens tends to absorb moisture from the air, and therefore does not take moisture from the eye. The latter characteristic is important because IOLs and contact lenses are often associated with the condition wherein the eye becomes excessively dry. While the coated lenses act like a humectant, insofar as they absorb moisture, they differ from a conventional humectant in that their properties are permanent. Moreover, the coated lenses absorb moisture without fogging.

The coating described above can also exist apart from its substrate. A free coating can be produced on a substrate to which the coating does not adhere permanently, and the coating can then be removed.

To produce such a free coating, one first proceeds as described above, to form the bilaminar non-fogging coating, on a clean, hard, and flat substrate such as glass. It may also be possible to use a substrate made of silicone or polypropylene. After the substrate has been coated, and grafting of the layers is completed, the coated panel must be soaked in water for a period of up to 24 hours. Then, the coating is removed by carefully scraping the substrate with a knife or sharp blade. The blade is used only to start the peeling. If the above steps are performed correctly, the coating comes off easily, and the result is a flexible material, similar in texture to cellophane, the material being entirely free of the substrate. The film can be formed into a roll, or folded, and then stored for later use.

An adhesive can be applied to one side of the free film described above, so that the film can be attached to a variety of different surfaces. By adhering the film produced according to the present invention, to a particular surface, one can impart a transparent, hydrophilic, non-fogging coating to virtually any object. This method is particularly advantageous when it is desired to coat a very large object which cannot be conveniently handled in the laboratory.

The coatings made according to the present invention are generally permanent; they do not become removed from their substrates. When the substrate is glass, one generally uses a "coupling agent", which is usually an organic compound of silicon, to enhance the adherence of the coating to the substrate. If a free coating is desired, it is necessary that the coating not adhere permanently to the substrate, and thus the coupling agent must be omitted.

Note also that if it is desired to form a free coating, it is necessary to use a flat substrate, so that the coating has an edge which is accessible to a blade. If the substrate is completely enveloped by the coating, it is not practical to remove the coating in the manner given above.

Although the invention has been described with respect to the preferred embodiments described above, it is possible to vary the invention in many ways, as will be apparent to those skilled in the art. Such variations should be deemed within the spirit and scope of the following claims.

What is claimed is:

1. A method of applying a transparent, hydrophilic, non-fogging coating to an object, the method comprising the steps of:
   a) coating the object with a solution of a polymer having a plurality of functional groups capable of chemically reacting with a mucopolysaccharide, and manifesting a high degree of adhesion to the object, wherein the solution includes about 0.1–10% ethylenedinitrilotetrakis-(2-hydroxypropane),
   b) removing solvent from said solution, so as to form a first continuous film,
   c) applying as a second coat an aqueous solution of a mucopolysaccharide, wherein the mucopolysaccharide solution includes about 0.1–5% ethylenedinitrilo-tetrakis-(2-hydroxypropane), the mucopolysaccharide solution also containing about 0.1–1% of desulfated heparin and about 0.1–5% of dimethyl sulfoxide,
   d) removing water from said second coat so as to form a second continuous film, and
   e) chemically joining said first and second films so as to effect an interlaminar graft, wherein both films retain their individual integrity.

2. The method of claim 1, wherein the amount of ethylenedinitrilotetrakis-(2-hydroxypropane) used in step (a) is about 1%.

3. The method of claim 1, wherein the amount of ethylenedinitrilotetrakis-(2-hydroxypropane) used in step (c) is about 1%.

4. The method of claim 1, wherein the amount of desulfated heparin used in step (c) is about 0.5%.

5. The method of claim 1, wherein the amount of dimethyl sulfoxide used in step (c) is about 1%.

6. The method of claim 1, wherein the joining step includes the of heating the films.

7. The product produced by the method of claim 1.

8. The product of claim 7, wherein the object is an intra-ocular lens.

9. The product of claim 7, wherein the object is a contact lens.

10. An object coated with a transparent, hydrophilic, non-fogging coating, the object having a surface, the coating including two continuous films joined together by an interlaminar graft, the first film being located adjacent to the surface, the second film being located adjacent to the first film, such that the first film is located between the surface and the second film, the first film including a polymer having a plurality of functional groups capable of chemically reacting with a mucopolysaccharide, and manifesting a high degree of adhesion to the object, the second film containing a mucopolysaccharide, wherein the first and second films also include ethylenedinitrilo-tetrakis-(2-hydroxypropane), the second film also containing desulfated heparin and dimethyl sulfoxide, wherein the amounts of the various coating constituents are present in effective amounts to produce said transparent, hydrophilic, non-fogging properties.

11. A lens having a transparent, hydrophilic, non-fogging coating, the coated lens being prepared by the steps of:
    a) coating the lens with a solution of a polymer having a plurality of functional groups capable of chemically reacting with a mucopolysaccharide, and manifesting a high degree of adhesion to the lens, wherein the latter solution includes about 0.1-10% ethylenedinitrilo-tetrakis-(2-hydroxypropane),
    b) removing solvent from said solution, so as to form a first continuous film,
    c) applying as a second coat an aqueous solution of a mucopolysaccharide, wherein the mucopolysaccharide solution includes about 0.1-5% ethylenedinitrilo-tetrakis-(2-hydroxypropane), the mucopolysaccharide solution also containing about 0.1−1% of desulfated heparin and about 0.1−5% of dimethyl sulfoxide,
    d) removing water from said second coat so as to form a second continuous film, and
    e) chemically joining said first and second films so as to effect an interlaminar graft, wherein both films retain their individual integrity.

12. The lens of claim 11, wherein the joining step comprises the step of heating the films.

13. The lens of claim 11, wherein the lens is an intra-ocular lens.

14. The lens of claim 11, wherein the lens is a contact lens.

15. A transparent, hydrophilic, non-fogging, flexible material, produced by the method comprising the steps of:
    a) coating an object with a solution of a polymer having a plurality of functional groups capable of chemically reacting with a mucopolysaccharide, and manifesting a high degree of adhesion to the object, wherein the latter solution includes about 0.1-10% ethylenedinitrilo-tetrakis-(2-hydroxypropane),
    b) removing solvent from said solution, so as to form a first continuous film,
    c) applying as a second coat an aqueous solution of a mucopolysaccharide, wherein the mucopolysaccharide solution includes about 0.1-5% ethylenedinitrilo-tetrakis-(2-hydroxypropane), the mucopolysaccharide solution also containing about 0.1-1% of desulfated herein and about 0.1-5% of dimethyl sulfoxide,
    d) removing water from said second coat so as to form a second continuous film,
    e) chemically joining said first and second films so as to effect an interlaminar graft, wherein both films retain their individual integrity, wherein the films together comprise a transparent, hydrophilic, non-fogging coating on the object, and
    f) removing said coating from the object to produce the flexible material.

16. The material of claim 15, wherein the joining step comprises the step of heating the object.

17. The material of claim 15, wherein the removing step comprises the steps of soaking the coating in water, and scraping the coating from the object with a sharp blade.

18. The material of claim 15, wherein the object has a surface which is clean and hard, and wherein the first and second films are formed on said surface.

19. A method of applying a transparent, hydrophilic, non-fogging coating to a surface, the method comprising the steps of preparing the flexible material of claim 15, applying an adhesive to a side of said material, and applying the adhesive-bearing side of said material to said surface.

* * * * *